United States Patent [19]

Burns

[11] 4,004,451
[45] Jan. 25, 1977

[54] AUTOMATED TIMING OF FLUID DELIVERY IN SAMPLE ANALYSIS

[75] Inventor: Donald A. Burns, Putnam Valley, N.Y.

[73] Assignee: Technicon Instruments Corporation, Tarrytown, N.Y.

[22] Filed: Dec. 24, 1974

[21] Appl. No.: 536,140

[52] U.S. Cl. .................................. 73/23; 137/3; 137/93
[51] Int. Cl.² .................................. G01N 31/00
[58] Field of Search ............... 137/93, 98, 8, 3; 73/194 E, 423 A, 194 R, 194 M, 19, 23; 250/302, 303

[56] References Cited
UNITED STATES PATENTS

| | | | |
|---|---|---|---|
| 2,780,414 | 2/1957 | De Heer | 137/98 X |
| 2,958,333 | 11/1960 | Poettmann | 137/8 X |
| 3,403,555 | 10/1968 | Versaci | 73/194 E |
| 3,435,659 | 4/1969 | Sternberg | 73/194 R |
| 3,435,660 | 4/1969 | Sternberg | 73/194 R |
| 3,435,678 | 4/1969 | Sternberg | 73/194 R |
| 3,600,953 | 8/1971 | Isreeli | 73/423 A |
| 3,621,715 | 11/1971 | Soderkvist | 73/194 E |
| 3,727,048 | 4/1973 | Haas | 250/302 |
| 3,739,636 | 6/1973 | Versaci | 73/194 E |
| 3,760,829 | 9/1973 | Schuck | 137/93 |
| 3,881,351 | 5/1975 | Prachar | 73/194 M |

Primary Examiner—Richard C. Queisser
Assistant Examiner—Stephen A. Kreitman
Attorney, Agent, or Firm—S. P. Tedesco; Stephen E. Rockwell

[57] ABSTRACT

Apparatus and method for analyzing liquid sample comprising flowing a stream including a liquid continuously in a conduit, detecting a flow rate characteristic in the conduit and generating a signal in response thereto, and increasing, decreasing or maintaining, unchanged the flow rate of the stream in the conduit in response to the signal, the flow being increased or decreased by the flow into the conduit of another fluid without changing the concentration of the aforementioned liquid. The continuing flow of the liquid may be the flow of a segmented sample-reagent liquid, and the other fluid which is added may be a gas.

17 Claims, 7 Drawing Figures

AUTOMATED TIMING OF FLUID DELIVERY IN SAMPLE ANALYSIS

BACKGROUND OF THE INVENTION

1. Field of the invention

This invention relates to apparatus and a method for controlling the volumetric flow rate in a conduit in a fluid sample analyzer of the automated type.

2. Prior art

Heretofore, each of a series of fluid samples flowing in a conduit seriatum having been divided into aliquot portions, each aliquot being treated differently for a different constituent of the sample, and subsequently each sample aliquot has been analyzed for the particular constituent in phased relation to every other aliquot, as in Skeggs et al U.S. Pat. No. 3,241, 432. In such an automated analyzer wherein the results of the analyses are displayed in real time, it is important that each aliquot reach analysis at the proper phased interval with reference to every other aliquot, and it has been noted that, on occasion, the various channels in such apparatus will slip out of phase due to such factors as temperature differences, viscosity differences and/or changes in tube diameter for example. In automated fluid sample analyzers proposed since the issuance of the aforementioned Skeggs et al U.S. Patent, it has been proposed, to avoid the problem by utilization of electronic components in electrical circuitry to provide a memory bank in which to store analytical data which may be recovered at intervals for suitable printout of the analytical results. In other words, the analyses are not made in real time. In many instances, the avoidance of this problem has added considerably to the cost of such fluid sample analyzer. It has been proposed to control the sequence of flow in analytical channels by a controller, such as a clock. However, such proposal has not overcome the problems attendant upon proper sequencing with reference to analysis such as discussed above.

In Pelavin U.S. Pat. No. 3,418,053, there is described a technique for detecting a characteristic in a fluid conduit of rate of flow therein, such as by photometric detection of an interface between a liquid and a gas. Such detection has generated a signal which has in some way affected the analytical process, such for example as deactivation of a recorder.

In Bannister et al, U.S. Pat. No. 3,756,459, there is disclosed analysis apparatus for metering a reagent for the periodic phased flow of the reagent in plural conduits from a common pressurized source. A valve controlling flow of a gas into one of the aforementioned conduits is closed by a controller periodically to permit flow of the reagent in the conduit from the pressurized source, flow of reagent in the conduit having previously been precluded by a same pressure of gas downstream in the conduit past the valve. By the same pressure, it is meant pressure the same as the pressure on the source. A photodetector downstream in the conduit detects a liquid-gas interface after commencement of the flow of the reagent and generates a signal to the controller to open the valve which once again stops the flow in the conduit from the source, and accelerates the segment of reagent down the conduit followed by the gas therein flowing past the open valve. No provision is made for proportionately increasing or decreasing the flow rate in response to the signal from the photodetection. The expressed purpose of the apparatus is to time the introduction of a predetermined volume of reagent into a volume of sample which sample volume is predetermined in some other manner.

SUMMARY OF THE INVENTION

One object of the invention is to provide a method and apparatus for analyzing liquid samples comprising flowing a stream including a liquid continuously in a conduit, detecting a flow rate characteristic in the conduit and generating a signal in response thereto, and increasing, decreasing or maintaining unchanged the flow rate of the stream in the conduit in response to the signal, the flow being increased or decreased by the flow into the conduit of another fluid without changing the concentration of the aforementioned liquid. The continuing flow of the liquid may be the flow of a segmented sample-reagent liquid, and the other fluid which is added may be a gas. Another object of the invention is to provide in a multichannel analyzer for various tests each associated with a corresponding channel for a constituent of interest in an aliquot of a sample, one of those divided among the channels, proper phasing of the channel with reference to the others in real time analysis for example. Further objects will be apparent for the following detailed description of the preferred embodiments of the invention.

DETAILED DESCRIPTION OF THE PREFERRED EMBODIMENTS

Figure 1:
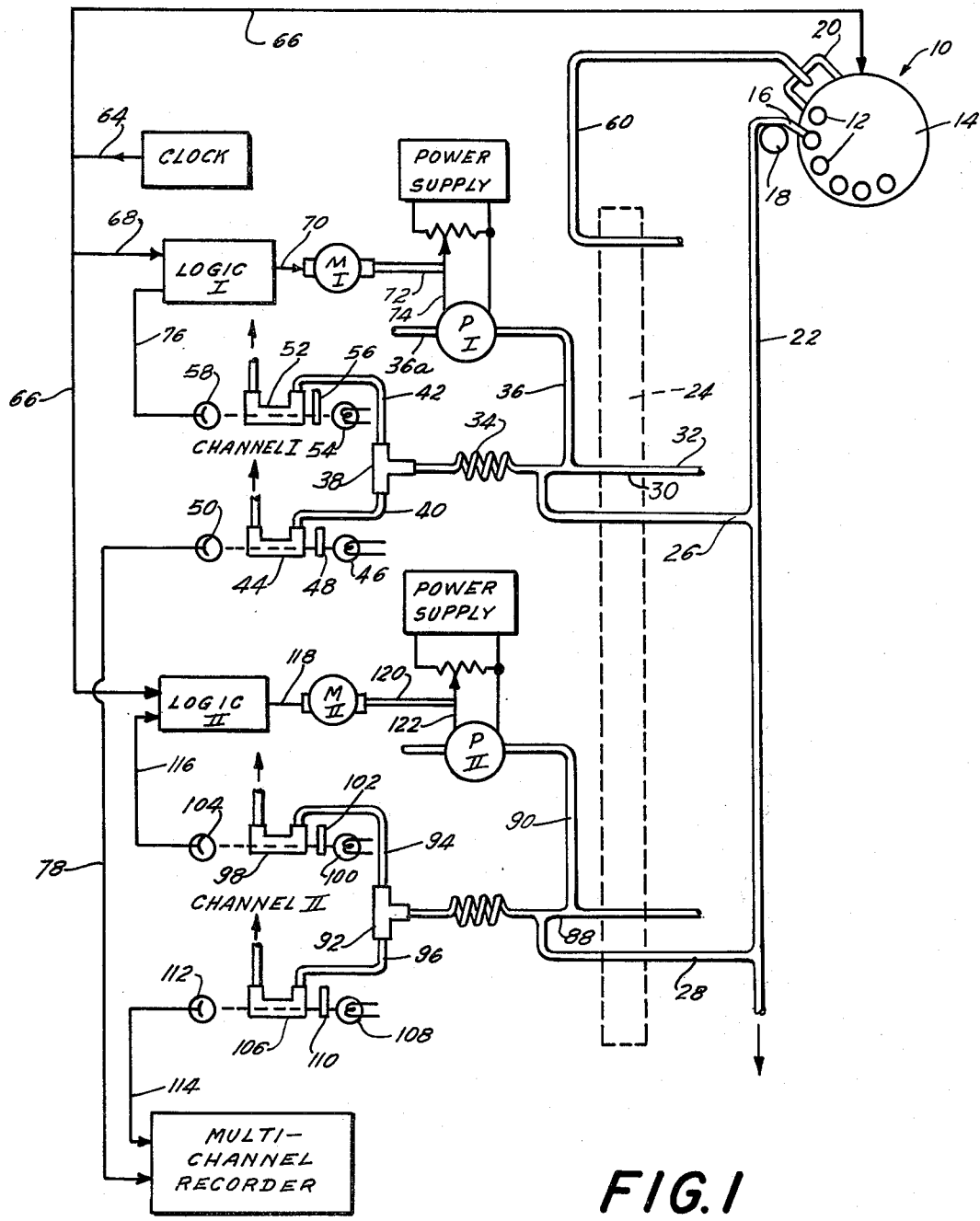
FIG. 1 is a schematic view illustrating automated timing of fluid delivery in sample analysis, embodying the invention.

In FIG. 1 there is shown a sampler, indicated generally at 10, to supply in this form a series of liquid samples for analysis seriatum. In the illustrated form, the samples may be a series of discrete blood serum samples, each of which samples is supported and confined in a cup 12 of a series of cups supported on a motor-driven turntable 14 of the sampler. Associated with the sampler is a conventional probe 16 provided on support 18 for movement of the probe into the cup 12 then indexed therewith for aspiration of the sample and then into the liquid within the wash receptacle 20 for aspiration of the wash liquid before the probe 16 enters the next sample cup after movement of the turntable 14. Between immersions in sample and wash liquids, the probe 16 aspirates air and the resultant stream flowing from the probe is segmented by segments of air and wash liquid, which segmentation of the sample stream preserves the integrity of the different samples. The segmentation is usually such that a wash liquid segment is located intermediate each sample slug and its neighbor, and an air segment is located between each wash liquid segment and the adjoining sample, all of which is conventional in continuous flow analysis instruments of the type described in de Jong U.S. Pat. No. 3,134,263.

The segmented stream flowing from probe 16 is conveyed therefrom to the coupled inlet end of a tube 22 through the action of a continuously operating pump 24 which may be of a conventional peristaltic type. The tube 22 has a compressible pump type branch 26 through which an aliquot of each sample flowing in the tube 22 is split and directed through such branch 26 through the pump 24 for analysis in channel I. The tube 22 in similar manner has a similar branch 28 through which another aliquot of the sample of the sample stream flowing through the tube 22 is directed through the pump 24 for analysis in channel II. To simplify the illustration and the description, the analyzer is shown as having only two channels, but it is to be understood that the analyzer may have a great many more channels such as 12, 20, or more.

Associated with channel I is a pump tube 30 extending through the pump 24 and having an inlet end connected to a non-illustrated source of a reagent such as Lieberman-Burchard reagent, the inlet end being indicated at 32. Intermediate the ends of the pump tube 30, the outlet end of the pump tube 26 Upstream of the coupling but downstream from the pump, the outlet end of a tube 36 is connected. The inlet end of the tube 36 is coupled to the outlet of continuously operating pump P I which has tube inlet 38 which may be exposed to the ambient atmosphere such as air, so that air is delivered from the pump to the aforementioned pump tube 30 in the form of bubbles which further segment the stream flowing in the tube 30. It is to be understood that, if desired, the variable speed pump P I may deliver any fluid to the stream flowing in tube 30 which is immiscible with the contents of the last mentioned stream, and which is also inert. Further, the output of the pump P I determines the flow rate in channel I.

The outlet end of tube 34 is coupled to one arm of a "T" connection or fitting 38 to provide an inlet thereto. Another arm of the fitting 38 is coupled to the inlet end of a tube 40 to which the greater part of the segmented sample-reagent stream is directed by the fitting 38, say, 90% of such stream by way of example. The remaining portion of the segmented sample-reagent stream flowing through the fitting 38 is outletted by the remaining arm thereof to the inlet end of tube 42. In the form of the invention being described with reference to channel I, the analysis is performed colorimetrically and the outlet end of the tube 40 is coupled with or without a debubbling device (none shown) to the inlet leg of flowcell 44 which has discharge leg directed to waste indicated at W. Channel I, may, for example, according to the previous discussion of channel I be for the determination of cholesterol in the sample aliquot directed therethrough. A light source 46 and a filter 48, as well as photodetector 50 are associated with flowcell 44 as shown in a conventional manner.

Further, in the form of the invention being described, there is provided a photometric sensor 52 to which the outlet of the tube 42 is connected, that is, to the inlet leg of flowcell 52. The flowcell or sensor 52 has associated therewith in the usual photometric manner, a light source 54, an appropriate filter 56, and a photodetector 58. The sensor 52 detects a dye in the wash liquid delivered from the receptacle 20 of the sampler, which dye is chosen so as not to interfere with any of the analyses performed and filter 56 is appropriate to the selected dye. The presence or absence of the dye at the sensor 52 is indicative of a flow rate characteristic in the tube 30. To supply the dye to the receptacle 20, compressible pump tube 60 extends through the pump 24 and has an inlet end connected to a non-illustrated source of such dye. The outlet end of the tube 60 is coupled to the reservoir 20 which reservoir has an overflow outlet to waste.

It is to be noted that in the form of FIG. 1, the sensor 52 and the cholesterol flowcell 44 are equidistant from the branch of the stream 34 into the tubes 40 and 42 so that the wash solution containing the dye reaches the sensor 52 concurrently with the dye reaching the cholesterol flowcell 44.

A programmer or clock determines when the dye should reach the sensor 52. The clock (FIG. 1) also controls the sampler 10 in the form shown. The clock has an output through lead 64 to a lead 66 in common with sampler 10 and having an input through lead 68 to logic I which has an output through lead 70 to motor I, the form of the last-mentioned output is dependent on whether the dye is early, late or on time in reaching the sensor 52. When the timing is correct, logic I concurrently receives a pulse from the clock and a pulse from the photodetector 58. Motor I is a reversible motor and has an output linkage 72 connected to the slidewire 74 of the potentiometer interposed between a power supply and the continuously operating pump P I. The output from the photodetector 58 associated with the sensor 52 is along lead 76 to an input of logic I. The output from the photocell 50 associated with the cholesterol flowcell 44 is along lead 78 to an input of a multichannel recorder such as utilized in aforementioned Skeggs et al U.S. Pat. No. 3,241,432.

Figure 2:
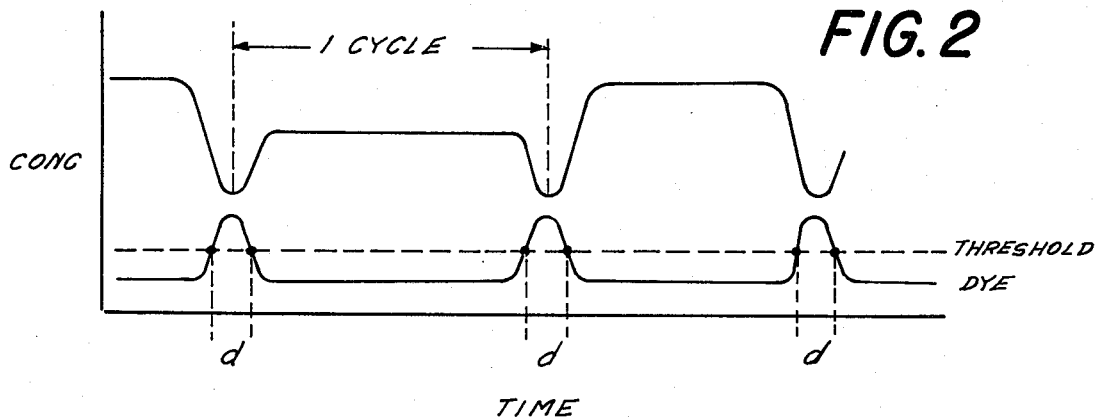
FIG. 2 is a flow diagram.
Figure 3:
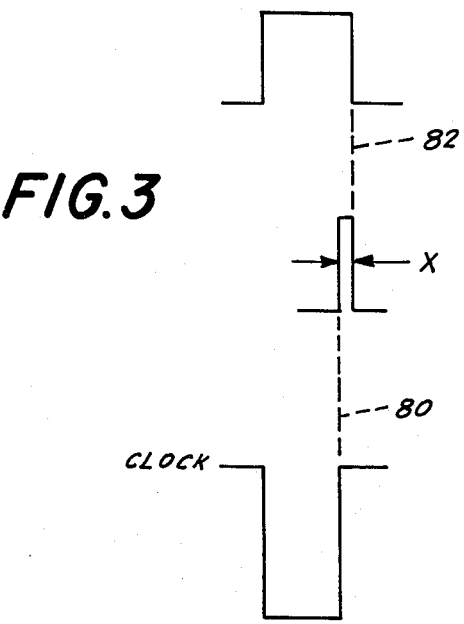
FIG. 3 is a timing diagram.

Turning now to the flow diagram of FIG. 2, the concentration of sample is minimal in the sensor 52 for each of a succession of samples at intervals d when the concentration M of the dye is at its maximum, and T indicates the threshhold at which the dye in the sensor 52 is sensed. Turning now to the timing diagram of FIG. 3, this diagram indicates the condition in which the signal 80 from the clock, is received by logic I earlier than the signal 82 from the photodetector 58, the difference between the signals or the lag in the flow in channel I being indicated by the interval X in this diagram. The output from logic I to motor I is in accordance with lag interval X to drive motor I forwardly sufficiently to move the potentiometer slidewire 74 through the linkage 72 to proportionately increase the speed of pump PI, so that a volume of air delivered from the pump PI to the fluid stream in the tube 30 is sufficient to increase the flow in the last-mentioned tube proportionately to eliminate the lag interval X.

Figure 4:
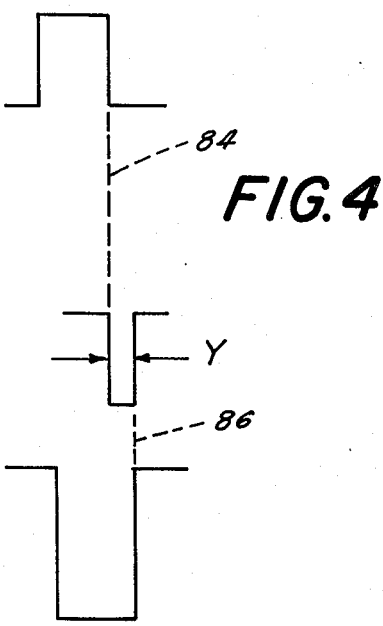
FIG. 4 is a timing diagram.

With reference to the timing diagram of FIG. 4, it will be noted that the signal 84 from the photodetector 58 to logic I indicates the presence of dye in the sensor 52 earlier than the signal 86 from the clock by an interval Y. In this case, the resulting signal from logic I to motor I serves to drive the motor I in the opposite direction to move the slidewire 74 of the potentiometer through the linkage 72 so that the speed of pump PI is decreased, resulting in less air being introduced into the stream in the tube 30 and thereby slowing the flow in the last-mentioned tube to eliminate the lead time Y in the flow of the fluid in the tube 30. It will be understood from the foregoing that if the pulse or signal from the clock is received by logic I currently with the signal from the photodetector 58, motor I is not energized. All this assures, with any necessary adjustment of the timing of the flow rate in the tube 30, that the treated sample aliquot will reach the flowcell 44 at the proper time interval with reference to all other treated aliquots in other channels, such as the channel II illustrated in FIG. 1. In other words, proper phasing of channels is effected in this manner.

Turning now to channel II shown in FIG. 1, this channel is a duplication of channel I and therefore need not be described in detail. Channel II may be for the quantitation of albumin in the sample aliquot directed thereto in tube 22 and the aforementioned compressible pump tube 28 having an inlet end connected to the tube 22. A compressible pump tube 88 extends through the pump 24 and has an inlet end thereof connected to a non-illustrated source of BCG reagent. Downstream of pump 24, the outlet end of tube 28 is couples to the tube 88 which tube 88 is similar to aforementioned tube 30. Air tube 90 has an outlet end coupled to the tube 88 in similar fashion which tube 90 is coupled to the outlet of pump P II, the last-mentioned pump having a tube inlet for an immiscible fluid such as air. It is understood that the pump P II is similar to the previously described pump P I and has associated therewith a power supply and a potentiometer so that the speed of pump P II may be increased and decreased with resulting increase or decrease of air delivered to the tube 88 for control of the flow rate in the last-mentioned tube. The tube 88 has an outlet connected to one arm of a "T" connection or fitting 92. The fitting 92, similar to the fitting 38, has outlets to tubes 94 and 96. The outlet of tube 94 is connected to the inlet leg of flowcell or sensor 98 similar to previously-described sensor 52. The outlet leg of the sensor 98 directs fluid to waste. The sensor 98 has associated therewith, in similar manner, a light source 100, an appropriate filter 102 for the dye and a photodetector 104.

The tube 96 has an outlet to the inlet leg of albumin flowcell 106 having an outlet leg directed to waste, the flowcell 106 having associated therewith in similar manner a light source 108 and appropriate filter 110 and a photodetector 112. The output from the photodetector 112 is through lead 114 to an input of the multichannel recorder to record analysis in real time. The output from the photodetector 101 associated with the sensor 98 is through a lead 116 to an input of logic II. Logic II also has an input from the clock through lead 66. Logic II has an output along lead 118 to reversible motor II. The output of motor II is through linkage 120 to slidewire 122 of the potentiometer between the power supply and the pump P II. The operation of channel II is identical to that of the previously described channel I. It will be understood that the aliquot which is treated and analyzed in channel II is received in a flowcell 106 and read subsequent to the reading of the flowcell 44 in channel I, due to the delay in the last-mentioned aliquot reaching the flowcell 106 occasioned by the longer distance which the last-mentioned aliquot has to travel to reach the flowcell 106 through the tubing including the tube 22.

Figure 5:
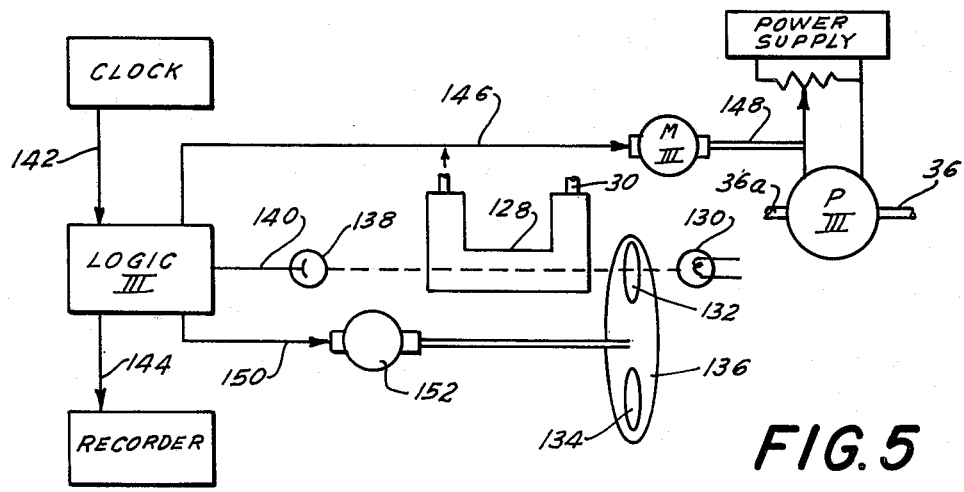
FIG. 5 is a fragmentary view illustrating a modification of the form of FIG. 1.

In the modified form of FIG. 5, the flowcell 128 serves the function of the previously described sensor 52 and also the function of the previously described flowcell 44 for quantitation of constituent of interest in a treated sample aliquot. In FIG. 5, there is shown pump tube 30 having an outlet directly into the inlet leg of the flowcell 128 which has an outlet leg for flow to waste. Associated with the combined sensor and flowcell 128 is a lightsource 130 to alternately direct light through diametrically opposed filter 132 and 134 of a filter wheel 136. The filter 132 is appropriate to detection of the aforementioned dye in the flowcell 128 while the filter 134 is appropriate to quantitation of the constituent of interest of the sample aliquot when it is present in the flowcell. In addition, there is in the lightpath a photodetector 138. The detector 138 has an output through lead 140 to an input of logic III which also has an input from the clock along lead 142. Logic III includes a switching device to switch the input along lead 140 to the output along lead 144 to the recorder when the constituent of interest of the sample aliquot is being measured in the flowcell 128. Logic III may have an output along lead 146, when such measurement is completed, to reversible motor III driving through linkage 148 the slidewire of a potentiometer interposed between the power supply and variable-speed air pump P III which is continually operated. During the interval that logic III is connected to the lead 146, logic III also has an output along lead 150 to a motor 152 to drive the filter wheel 136 to a position so that the filter 132 is in the sight path between the light source 130 and the photodetector 138. Though not illustrated, the output on the pump P III, like the described output of pump P I, is operative to slow, increase or leave unchanged the flow in the tube 30 to the flowcell 138.

Figure 6:
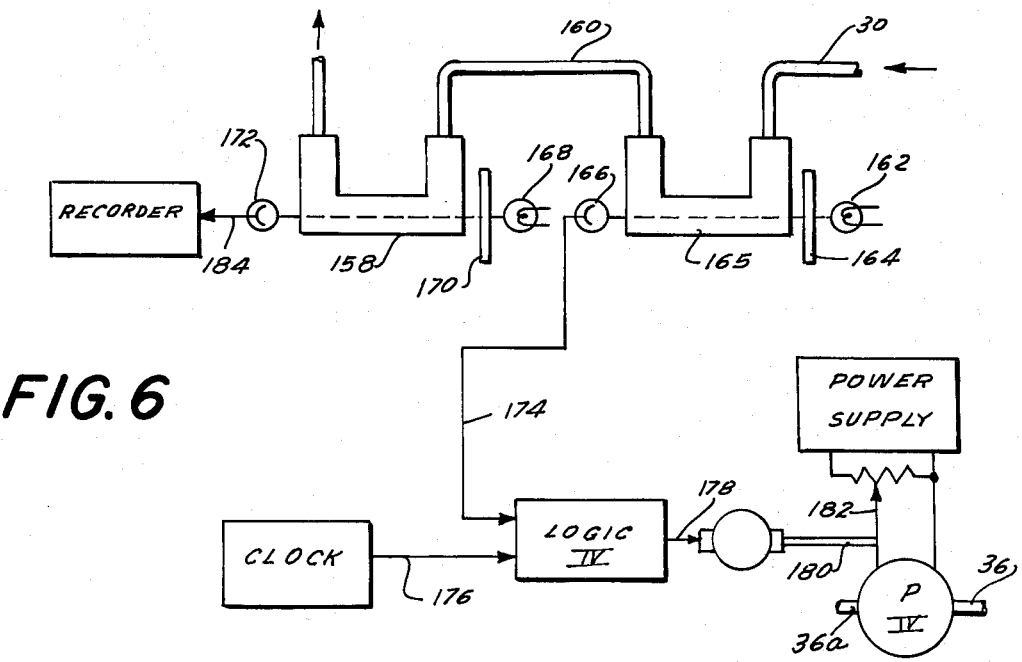
FIG. 6 is a fragmentary view illustrating a further modification of the form of FIG. 1.

In the modification shown in FIG. 6, the outlet end of the tube 30 is connected directly to the inlet leg of flowcell or sensor 156 which is arranged in tandem with respect to a flowcell 158 in which the constituent of interest of the treated aliquot flowing in tube 30 is quantitatively measured. The flow from the outlet leg of the sensor 156 is to the inlet of tube 160 which has the outlet thereof connected to the inlet leg of the flowcell 158 the outlet leg of which directs the fluid to waste. Associated with the sensor 156 is a light source 162 and a filter 164 appropriate to detection of the dye in the stream, and a photodetector 166. In similar fashion, the flowcell 158 has a light source 168, a filter 170 appropriate to the quantitation of the constituent of interest in the sample aliquot and a photodetector 172. The photodetector 166 associated with the sensor 156 has an output through lead 174 to an input of logic IV which has an input from the clock along a lead 176. Logic IV has an output along lead 178 to reversible motor IV which actuates, through a linkage 180, slidewire 182 of a potentiometer interposed between a power supply and variable speed air pump P IV continuously operated. As in the previously described forms, the pump has a fluid output not illustrated to tube 30 so that the continuously operating pump P IV may increase, decrease, or leave unchanged the flow rate of the segmented stream in the tube 30 for proper phasing of the analysis conducted in flowcell 158 in relation to other analysis channels not shown. The delay in the flow of the stream from the sensor 156 to the flowcell 158 through the tube 160 is allowed for by logic IV. The photodetector 172 associated with the flowcell 158 in which is conducted the quantitation of the treated sample aliquot has an output through lead 184 to an input of the multichannel recorder.

Figure 7:
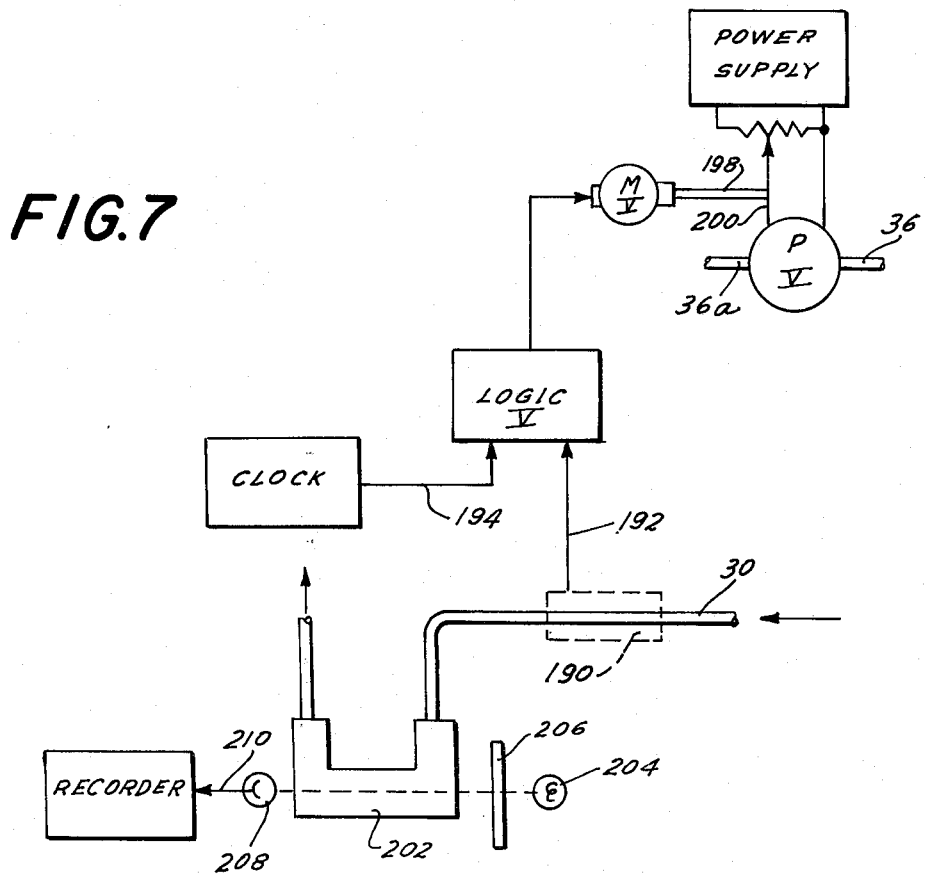
FIG. 7 is a fragmentary view illustrating another modification of the form of FIG. 1.

In the modified form of FIG. 7, there is interposed in the tube 30 a detector 190 for detection of a radioactive or florescent substance. In this illustrated form, a radioactive substance is substituted for the dye which is periodically introduced into the wash solution delivered by the non-illustrated sampler in like manner to the dye in the wash solution. The sensor or detector 190 which detects such substance in the periodic flow thereof has an output along lead 192 to an input of logic V which also receives an input from the clock along lead 194 to an input thereof. Logic V has an output along lead 196 to reversible motor V which through a linkage 198 drives the slidewire 200 of a potentiometer interposed between the power supply and continually operated a variable speed air pump P V. As in the other forms described previously, though not illustrated in FIG. 7, the pump P V has an output to the tube 30 for increasing, or decreasing or leaving unchanged the flow rate of the segmented stream in the tube 30 to effect the arrival of a treated sample aliquot at a flowcell 202 in proper timed relation to other non-illustrated channels. The tube 30 has an outlet directly to the inlet leg of the flowcell 202 which has an outlet leg to direct fluid to waste. The flowcell 202 for quantitation of the constituent of interest of the sample aliquot has associated therewith in the usual manner a light source 204, an appropriate filter 206 and a photodetector 208. The photodetector has an output along lead 210 to the multichannel recorder.

It is believed made clear from the foregoing that in all illustrated forms of the invention the wash solution carries the substance, e.g. a dye, a radioactive or a florescent substance and that the wash solution segment associated with each sample serves the function not only of isolating the sample from another with its associated gas segments but serves also to cleanse the walls of the tubing to prevent intercontamination of the samples. Further, it will be apparent, particularly with reference to FIG. 1, that in a multichannel analyzer embodying the invention, the flow rates in plural channels are regulated one to the other, and in the form of FIG. 1 all are dependent on the controller or clock for the phasing of the channels. Moreover, it is made clear than in achieving automatically relative adjustments of the flow rates in the channels of such an anlyzer the flow rates are forced to conform to the periodic signals from a controller such as a clock. Obviously, the analysis may be other than a photometric analysis, such as a potentiometric analysis, for example.

Further, it will be appreciated that the invention, as previously characterized, does in fact, provide flowing a stream including a liquid continuously in a conduit, detecting a flow rate characteristic in the conduit and generating a signal in response thereto, and increasing, decreasing or retaining unchanged the flow rate of the stream in the conduit in response to the signal, the flow being increased or decreased by the flow into the conduit of another fluid without changing the concentration of the aforementioned liquid. For the purpose of placing a construction on the appended claims, it is to be understood that the reference to "another fluid" means a fluid other than the aforementioned liquid but does not exclude a fluid other than the liquid, such as any gas present in segments thereof in the fluid stream.

While several forms of the automated timing of fluid delivery in sample analysis have been illustrated and described, it will be apparent, especially to those versed in the art, that the invention may take other forms and is susceptible to changes in details without departing from the principles of the invention.

What is claimed is:

1. A method for quantitatively analyzing a constituent of a liquid sample, comprising:
    flowing in a first conduit portion toward a second conduit portion a stream including said sample at a constant volumetric rate;
    introducing at a volumetric rate continually another fluid into the stream in said first conduit portion:
    determining the velocity of said stream in one of said conduit portions and generating a signal in response thereto:
    proportionately varying said volumetric rate of said introduction of said other fluid into said first conduit portion in response to said signal to control the dwell time of said sample in said conduit portion: and
    analyzing said sample constituent in said second conduit portion.

2. A method as defined in claim 1, wherein: said flowing of said stream in said first conduit portion comprises periodically introducing into said stream a volume of a third substance, and said determination of the velocity of said stream comprises detecting said third substance at a station located at a position along the length of said conduit.

3. A method as defined in claim 1, wherein: said sample comprises an aliquot of a sample and further including flowing a second aliquot of said sample in such a stream in a third conduit portion toward a fourth conduit portion for a different analysis, and correlating the flow in said fourth conduit portion with respect to the flow in said second conduit portion.

4. A method as defined in claim 1, wherein: said introduction of said other fluid into said first conduit portion comprises flowing gas thereinto.

5. A method as defined in claim 1, wherein: said flowing of a stream in said first conduit portion comprises flowing a gas segmenting said sample.

6. A method as defined in claim 3, wherein: said correlation of said flow rate in said second and fourth conduit portions comprises introducing at a volumetric rate continually said other fluid into said third conduit portion, determining the velocity of said stream in one of said third and fourth conduit portions and generating a signal in response thereto, and proportionately varying said volumetric rate of introduction of said other fluid into said third conduit portion in response to said signal.

7. A method as defined in claim 3, wherein: said correlating of said flow rates of said streams in said second and fourth conduit portions comprises phasing the flow of said streams.

8. A method as defined in claim 1, including: flowing a stream of a series of said samples sequentially in said first conduit portion in isolated condition from one another, and varying said volumetric rate of said introduction of said other fluid into said first conduit portion in response to said signal to control the respective dwell times of said samples in said second conduit portion.

9. A method as defined in claim 8, wherein: said samples are isolated by wash solution segments intermediate said samples, and said determination of the velocity of the stream includes detecting said wash solution segments.

10. Apparatus for quantitatively analyzing a constituent of a liquid sample, comprising:
    means flowing in a first conduit portion toward a second conduit portion a stream including said sample at a constant volumetric rate;
    means introducing at a volumetric rate continually another fluid into the stream in said first conduit portion;

means determining the velocity of said stream in one of said conduit portions and generating a signal in response thereto;

means proportionately varying said volumetric rate of introduction of said other fluid into said first conduit portion to control the dwell time of said sample in said second conduit portion; and means analyzing said sample constituent in said second sample portion.

11. Apparatus as defined in claim 10, wherein: said means flowing a stream in said first conduit portion includes means periodically introducing into said stream a volume of a third substance, and said determination means comprises means detecting third said substance at a station located at a position along the length of said conduit.

12. Apparatus as defined in claim 10, wherein: said sample comprises an aliquot of a sample, and further including means flowing a stream including a second aliquot of said sample in a third conduit portion towards a fourth conduit portion for a different analysis in the latter, and means correlating the flow rate of said fourth conduit portion with respect to the flow rate in the second conduit portion.

13. Apparatus as defined in claim 10, wherein: said means introducing said other fluid into said first conduit portion comprises means introducing a gas into said first conduit portion.

14. Apparatus as defined in claim 12, wherein: said means correlating the flow rate in said fourth conduit portion with respect to the flow in said second conduit portion comprises means introducing said other fluid at a volumetric rate continually into said third conduit portion, means determining the velocity of said stream in one of said third and fourth conduit portions and generating a signal in response thereto, and means proportionately varying said rate of introduction of said other fluid into said third conduit portion in response to said signal.

15. Apparatus as defined in claim 12, wherein: said means correlating the flow rate in said second and fourth conduit portions comprises means phasing the flow in said second and fourth conduit portions.

16. Apparatus as defined in claim 10, wherein: said means flowing a stream in said first conduit portion flows a series of said samples in isolated condition from one another, and said means varying said rate of said introduction of said other fluid first conduit portion controls the respective dwell times of said samples in said second conduit portion.

17. Apparatus as defined in claim 16, wherein: said means introducing said samples introduces said samples isolated from each other by wash solution segments intermediate said samples, and said means determining the velocity of the stream includes means detecting said wash solution segments.

* * * * *